United States Patent [19]

Meszaros

[11] Patent Number: 5,026,932
[45] Date of Patent: Jun. 25, 1991

[54] PREPARATION OF 4-BROMO-O-XYLENE IN LIQUID SULFUR DIOXIDE

[75] Inventor: Mark W. Meszaros, Batavia, Ill.

[73] Assignee: Amoco Corporation, Chicago, Ill.

[21] Appl. No.: 484,341

[22] Filed: Feb. 22, 1990

[51] Int. Cl.$^5$ ............................................. C07C 17/12
[52] U.S. Cl. ................................... 570/206; 570/207; 570/209
[58] Field of Search ......................... 570/206, 207, 209

[56] References Cited

U.S. PATENT DOCUMENTS 2,452,154  10/1948  Ross ..................................... 570/206
3,932,542   6/1976  Gerns .................................... 570/206

FOREIGN PATENT DOCUMENTS 1411524  10/1975  United Kingdom ................. 570/206

OTHER PUBLICATIONS

Meirovics et al., "Chemical Abstracts" vol. 74 (1971) 42032v.

Canselier, Bull. Soc. Chim. France (1972) pp. 762–764.
Canselier, Bull. Soc. Chim. France (1971) pp. 1785 and 1788.

*Primary Examiner*—Werren B. Lone
*Attorney, Agent, or Firm*—Thomas E. Nemo; William H. Magidson; Ralph C. Medhurst

[57] ABSTRACT

A regioselective process is provided for preparing 4-bromo-o-xylene in an isomer mixture of 4-bromo-o-xylene and 3-bromo-o-xylene by combining bromine with o-xylene in liquid sulfur dioxide medium. A bromine to o-xylene mole ratio of about 0.4:1 to about 1:1 is utilized at a temperature in the range of about $-20°$ C. to about $40°$ C. While preferred temperatures are in the about $-15°$ C. to about $-9°$ C. range, temperatures above about $-9°$ C. can be used by maintaining the reactant solution under pressure. A product isomer mixture can be isolated by vacuum distillation. A 92:8 weight ratio mixture of 4-bromo-o-xylene and 3-bromo-o-xylene is thus obtainable.

13 Claims, No Drawings

PREPARATION OF 4-BROMO-O-XYLENE IN LIQUID SULFUR DIOXIDE

FIELD OF THE INVENTION

This invention relates to regioselective bromination of o-xylene to prepare 4-bromo-o-xylene in liquid sulfur dioxide as the reaction medium.

BACKGROUND OF THE INVENTION

4-Bromo-o-xylene is a useful starting reagent in some syntheses of riboflavin (vitamin $B_2$). Moreover, 4-Bromo-o-xylene can be used for the preparation of diphenyl ethers, such as 3,3',4,4'-tetramethyldiphenyl ether, 1,4-bis(3,4-dimethylphenoxy) benzene, and the like.

4-Bromo-o-xylene can be prepared by reacting 3,4-dimethylaniline with $CuBr_2NO$, but such a preparation procedure is relatively costly, and is impractical on a large scale.

A route for commercial scale preparation of 4-bromo-o-xylene involves the addition of bromine ($Br_2$) to o-xylene. However, when one follows the solvent-less preparation procedure described in "Organic Syntheses", Vol. 3, pp 138, 139 (1955):

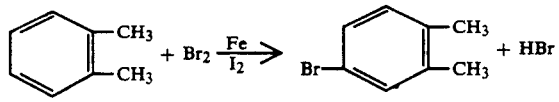

wherein the mole ratio of bromine to o-xylene is 0.875 and the reaction temperature is 0° to −5° C., it is found by analysis that this procedure produces a 75:25 weight ratio mixture of 4-bromo-o-xylene to 3-bromo-o-xylene.

The produced bromo-o-xylene isomers are extremely difficult to separate because they have virtually the same boiling point (214° C. for 4-bromo-oxylene compared to 215° C. for 3-bromo-o-xylene). These isomers also cannot be separated by crystallization. Separation by gas chromatography is also difficult. A capillary G.C. column with cyanopropyl methyl silicone coating is needed to separate these particular isomers. It is therefore desirable to synthesize 4-bromo-o-xylene in as high a purity as possible to minimize the quantity of admixed 3-bromo-o-xylene present.

J.P. Canselier has reported (Bull.Soc.Chim. France, 1972, pp. 762–764, and Bull.Soc.Chim. France, 1971, pp. 1785–1788) achieving a 93.4:6.5 mixture of 4-bromo-o-xylene to 3-bromo-o-xylene by reacting a mixture of bromine, and o-xylene in $SO_2$ solution. The procedure for achieving a 93.4:6.5 mixture of 4-bromo-o-xylene to 3-bromo-o-xylene is not given but it is stated that it was run according to a process described for toluene, i.e., a mixture of bromine and sulfur dioxide is added to a very dilute mixture of the hydrocarbon at −40° C. and in a darkened reactor. The resulting mixture is then agitated at −9° C. for 3 hours before the sulfur dioxide is removed and the product isolated by distillation. His procedure is not suitable for commercial scale preparation of 4-bromo-o-xylene in high yields.

A process that can produce 4-bromo-o-xylene from relatively low cost starting materials in relatively high yield and in combination with a minimal amount of 3-bromo-o-xylene and other by-products would have commercial importance. The present invention provides such a process.

SUMMARY OF THE INVENTION

A regiospecific process for producing an isomer mixture rich in 4-bromo-o-xylene is provided wherein bromine is combined with o-xylene in a liquid sulfur dioxide medium within a bromine-to-o-xylene mole ratio range of about 0.4:1 to about 1:1, respectively. The sulfur dioxide to oxylene mole ratio range is at least about 1:1 but no more than about 20:1. The resulting reactant admixture is maintained at a temperature in the range of about −20° C. to about 40° C. during the reaction.

The use of sulfur dioxide as a solvent for the bromination of o-xylene produces much greater regioselectivity favoring 4-bromo-o-xylene production than other known solvents or catalysts. It also decreases the bromination of aromatic side chains. Unlike other bromination processes, the bromination reaction using sulfur dioxide can be run in the presence of actinic radiation without significant formation of alpha-bromo-o-xylene. Relatively high yields of 4bromo-o-xylene are obtained.

It is presently preferred to employ a bromine ($Br_2$) to o-xylene mole ratio in the range of about 0.7:1 to about 0.95:1, a sulfur dioxide to o-xylene ratio in the range of about 2:1 to about 20:1, and a reaction temperature in the range of about −9° C. to about −15° C. Preferably, the bromine is slowly added to a sulfur dioxide solution of the o-xylene with agitation, and, after such addition is completed, the agitation is continued for a period of time to complete the reaction.

The product isomer mixture is separable from the reaction product by vacuum distillation.

Various other and further features, embodiments, and the like which are associated with the present invention will become apparent and better understood to those skilled in the art from the present description.

DETAILED DESCRIPTION OF PREFERRED EMBODIMENTS

The bromination reaction of the present invention is carried out in liquid phase utilizing sulfur dioxide as the reaction medium. Bromine ($Br_2$) is combined with o-xylene in liquid sulfur dioxide within a bromine to o-xylene mole ratio range of about 0.4:1 to about 1:1, respectively, and within a sulfur dioxide to o-xylene mole ratio range of at least about 1:1 while maintaining the resulting admixture at a temperature in the range of about −20° C. to about 40° C.

A presently preferred such mole ratio of bromine to o-xylene is about 0.7:1 to about 0.95:1, a presently preferred mole ratio of sulfur dioxide to o-xylene is about 2:1 to about 20:1, and a presently preferred reaction temperature is in the range of about −9° C. to about −15° C.

If desired, a Lewis acid catalyst, such as an iron halide, can be used; however, a clear advantage of such a catalyst has not been demonstrated as compared to conducting this reaction in the absence of such a catalyst. If employed, a catalytically effective amount of such catalyst is used. For example, a suitable amount of such catalyst is in the range of about 0.01 to about 0.1 equivalents of such catalyst per equivalent of o-xylene.

Each of the o-xylene and the bromine can be preliminarily dissolved in the sulfur dioxide, if desired, or one or the other of such reactants can be preliminarily so dissolved and the other of such reactants can be added directly thereto with stirring. A present preference is to add bromine to a solution of o-xylene in sulfur dioxide.

The use of sulfur dioxide as a bromination reaction medium for o-xylene provides, among other benefits, at least a suppression, and sometimes even prevention, of by-product alpha-bromo-o-xylene production.

Alpha-bromo-o-xylene is a generally undesirable by-product since not only does it reduce yields of the desired 4-bromo-o-xylene based on starting o-xylene, but it also is difficult to separate by distillation. Alpha-bromo-o-xylene has a similar boiling point (217° C.) to that of 4-bromo-o-xylene and 3-bromo-o-xylene.

For example, when o-xylene is brominated under solvent-less conditions at −10° C. without blackening the reaction flask or trying to keep all actinic radiation (e.g., light) out, up to about 10 percent alpha-bromo-o-xylene is produced. Under identical conditions, except for the use of $SO_2$ as a solvent, only about 0.3 percent alpha-bromo-o-xylene is produced.

In addition to reducing the amount of alpha-bromo-o-xylene formed, the use of sulfur dioxide as a solvent for o-xylene, bromine, and bromo-o-xylene isomers is particularly desirable because it produces relatively greater regioselectivity favoring 4-bromo-o-xylene production than other solvents or catalysts. Sulfur dioxide also decreases the bromination of aromatic side chains and aids in achieving high yields of 4-bromo-o-xylene.

Sulfur dioxide refluxes (boils) at about −9° C. at atmospheric pressure Such a temperature constitutes a particularly convenient reaction temperature for practicing the process of this invention. When the reaction is carried out at more elevated temperatures, the reaction zone can be maintained under autogenous pressures to maintain $SO_2$ in a liquid state. Pressures up to about 4 atmospheres are convenient. At 0° C. the $SO_2$ vapor pressure is about 20 psig, and at ambient temperature, about 40 psig.

At the end of a given reaction of bromine with o-xylene, and before a subsequent purification of a resulting liquid reaction product mixture, the sulfur dioxide can be easily separated by warming a product solution to vaporize the sulfur dioxide and venting same. Any by-product HBr produced in this reaction can be concurrently removed.

While any admixing technique can be employed for the bromine and o-xylene, it is presently preferred to slowly add, with stirring, the bromine to the o-xylene dissolved in liquid sulfur dioxide. Preferably, the o-xylene is dissolved in the sulfur dioxide first and the bromine is then slowly added thereto with stirring. A presently preferred bromine addition rate is about 0.5 to about 2.5 moles of bromine per hour per mole of o-xylene. More preferably, the rate is about 0.7 to about 1.5 moles of bromine per hour per mole of o-xylene.

After the admixture of bromine with o-xylene is complete, it is presently preferred to continue to agitate the reaction mixture at a temperature within the range indicated to optimize the conversion of the starting reactants. The post-addition agitation time period is about 0.05 to about 1 hour with such time period more preferably being at least about 0.08 hour, but not more than about 0.5 hour.

It is presently preferred that each of the reactants, and also each of the other components present in a reaction, such as liquid sulfur dioxide (if employed), or catalyst (if employed), have a purity of at least about 95 weight percent, and more preferably a purity of at least about 99 weight percent, so as to enhance yields of 4-bromo-o-xylene. For example, if a small amount of m-xylene is present with the o-xylene, as is common in many commercially available o-xylenes, the m-xylene reacts with the bromine to produce a small amount of 4-bromo-m-xylene which necessarily reduces the yield of 4-bromo-o-xylene.

Thus, by using liquid sulfur dioxide as a solvent, a maximized production or yield of an isomer mixture of 4-bromo-o-xylene and 3-bromo-o-xylene appears to result without appreciable by-product formation. For example, production of alpha-bromo-xylene is suppressed, as hereinabove explained. Such yields are achieved when the reactant mole ratio of bromine ($Br_2$) to o-xylene is within the preferred range above indicated, and the solution temperature is within the preferred range above indicated. Using the preferred slow addition, with continuous stirring, of bromine to o-xylene within the preferred mole ratio range above indicated and with the bromine addition rate being in the range above indicated, and with agitation being continued after bromine addition for a time within the preferred range above indicated, various weight ratios of 4-bromo-o-xylene to 3-bromo-o-xylene can be obtained which are usually in the range of about 80:20 to about 92:8. The yields of 4-bromo-o-xylene based on starting o-xylene are desirably high, being commonly in the range of about 60 to about 85 percent (based on o-xylene).

Product isomer mixtures of 4-bromo-o-xylene and 3-bromo-o-xylene are isolatable from a liquid reaction product by vacuum distillation.

The exact preparation conditions and procedure used, such as the mole ratio of $Br_2$ to o-xylene, the reaction temperature, the mixing procedure, and other variables affect the quantity of 4-bromo-o-xylene produced and the yields thereof achieved. A typical yield of 4-bromo-o-xylene is illustrated by Example 1 below.

The following examples are offered to specifically illustrate the invention. These examples are not to be construed as limiting the scope thereof, however.

In the examples, "4-BOX" designates 4-bromo-oxylene, "3-BOX" designates 3-bromo-o-xylene, "4-BMX" designates 4-bromo-m-xylene, "A-BOX" designates alpha bromo-o-xylene, "DiBOX" designates dibromo-o-xylene, "4:3-BOX" designates weight ratio of 4-bromo-o-xylene to 3-bromo-o-xylene, "o-X" designates o-xylene, "$Br_2$" designates bromine, "T" designates temperature in degrees centigrade, and "o-X Conc." designates molar concentration of o-xylene reactant in $SO_2$.

EXAMPLE 1

Addition of $Br_2$ to o-X in $SO_2$

A 2.5 molar solution of o-X (70 g, 0.66 mol) in liquid $SO_2$ (305 g, 257 ml) was prepared in a 500 ml three neck flask equipped with a dry ice condenser, addition funnel, and a stopcock adapter. The solution was kept at $SO_2$ reflux temperature (about −10° C.) $Br_2$ (82.1 g, 49 ml, 0.51 mol) was added through the addition funnel at about 1 ml/min (or about 0.92 moles of $Br_2$ per hour per mole of o-X) for a total addition time period of about 50 minutes. At the end of such addition, the mole ratio of $Br_2$ to o-X was thus 0.77. After the $Br_2$ was thus added, the reaction mixture was further continuously stirred for ten minutes after which the $SO_2$ was removed by evaporation. After vacuum distillation, an isomer mixture of 92:8 weight ratio of 4-BOX to 3-BOX was isolated.

EXAMPLES 2-10

Reaction of Bromine with o-Xylene in Sulfur Dioxide

A series of o-xylene brominations in sulfur dioxide was performed in the following manner: A 100 ml three neck flask was equipped with a dry ice bath cooled to −78° C. with a dry ice/acetone mixture. The liquid $SO_2$ was added through the stopcock adapter. After the addition was complete, the $SO_2$ was warmed to −15° C., and o-xylene was added through the addition funnel and dissolved in the sulfur dioxide. The bromine was then added slowly with continuous stirring at a rate estimated to be about 1.0 to about 1.5 moles bromine per hour per mole of o-xylene (usually over a time interval of about 30 min.) through the addition funnel. The reaction solution was kept at −15° C. using a cold bath. The reaction solution was continuously stirred after such addition for an additional 10 min. at −15° C. before the solution was warmed and the $SO_2$ removed by evaporation. Table I below shows the results.

In Example 9, a Fischer-Porter bottle was filled with $SO_2$ (62 g, 41 ml) and o-xylene (8 g, 75 mmol) and cooled to 0° C. with an ice water bath. The pressure was 20 psig due to the $SO_2$ partial pressure at that temperature. The bromine (9 g, 56 mmol) was slowly added and the reaction stirred for an additional 10 min. after the addition was complete. The resulting isomer mixture of bromo-o-xylene was 90:10 4-BOX:3-BOX.

In Example 10, a Fischer-Porter bottle was filled with $SO_2$ (53 g, 35 ml) and o-xylene (10 g, 94 mmol) and placed in a water bath at 20° C. The pressure was 43 psig due to the $SO_2$ partial pressure at that temperature. The bromine (7 g, 44 mmol) was slowly added and the reaction stirred for an additional 10 min. after the addition was complete. The resulting isomer mixture of bromo-o-xylenes was 90:10 4-BOX:3-BOX.

In Example 3, the 4-BOX:3-BOX product obtained was isolated. After the $SO_2$ and HBr were removed by evaporation, the reaction product was washed with 0.1 N aqueous NaOH solution (250 ml), and twice with $H_2O$ (125 ml each). The organic layer was dried over $MgSO_4$. No further purification was necessary. The isolated yield was 75 g (405 mmol, 80 percent yield).

Separation of 4-bromo-o-xylene from 3-bromo-o-xylene in an isomer mixture was accomplished using a Hewlett Packard 5890 gas chromatograph equipped with a 50 m by 0.25 mm inside diameter CPS-1 capillary column which contains a cyanopropyl methyl silicone film.

The most effective temperature program was an initial temperature of 100° C. followed by a 4° C. per minute temperature increase up to 180° C. final temperature.

Reaction products were identified by (a) gas chromatography - mass spectroscopy; and (b) comparison of retention times with that of authentic samples. Also, $^1H$ and $^{13}C$ NMR (nuclear magnetic resonance) were used to verify the structure of 4-BOX.

The foregoing specification is intended as illustrative and is not to be taken as limiting. Still other variations within the spirit and the scope of the invention are possible and will readily present themselves to those skilled in the art.

We claim:

1. A regioselective process for producing a mixture rich in 4-bromo-o-xylene comprising combining bromine with o-xylene in liquid sulfur dioxide and within a bromine-to-o-xylene mole ratio range of about 0.4:1 to about 1:1, respectively, and within a sulfur dioxide to o-xylene mole ratio range of at least about 1:1 but no more than about 20:1 while maintaining the resulting admixture at a temperature in the range of about −20° C. to about 40° C. to produce a product mixture.

2. The process of claim 1 wherein said sulfur dioxide to o-xylene mole ratio range is about 2:1 to about 20:1, respectively.

3. The process of claim 1 wherein said bromine to o-xylene mole ratio range is about 0.7:1 to about 0.95:1.

4. The process of claim 3 wherein said combining is carried out by admixing said bromine with a sulfur dioxide solution of said o-xylene.

5. The process of claim 4 wherein said bromine is combined with said sulfur dioxide solution at an addition rate in the range of about 0.5 to about 2.5 moles of bromine per hour per mole of o-xylene to produce said admixture.

6. The process of claim 5 wherein said admixture is further agitated for a period of time of about 0.05 to about 1 hour to produce a product mixture.

7. The process of claim 1 wherein said temperature range is about −15° C. to about −9° C.

8. The process of claim 1 wherein said temperature range is above about −9° C. and said admixture is maintained under autogenous pressure.

9. The process of claim 1 wherein the produced product admixture is warmed to an extent sufficient to evaporate said sulfur dioxide and produce a liquid reaction product.

10. The process of claim 1 wherein said liquid reaction product is subjected to vacuum distillation to isolate said isomer mixture.

11. The process of claim 1 wherein said combining is carried out in the presence of a catalytically effective amount of a Lewis acid catalyst.

12. The process of claim 10 wherein said isomer mixture is passed through a capillary gas chromatograph column which has been precoated with cyanopropyl methyl silicone to separate 4-bromo-o-xylene.

13. The process of claim 1 wherein said sulfur dioxide to o-xylene mole ratio range is about 1:1 to about 13:1, respectively.

TABLE I

| | Summary of Data for Examples 2-10 | | | | | | | | | | | | | | |
|---|---|---|---|---|---|---|---|---|---|---|---|---|---|---|---|
| | GC Analysis - Area % | | | | | Weight Ratio | Mole Ratio | grams | | | mmol | | ml liq. | o-X Conc., | |
| Ex. No. | 4-BMX | 3-BOX | 4-BOX | A-BOX | DiBOX | 4:3-BOX | $Br_2$/o-X | o-X | $Br_2$ | $SO_2$ | o-X | $Br_2$ | $SO_2$ | M | T, °C. |
| 2 | 1.1 | 7.3 | 86.4 | — | 2.65 | 92:8 | 1 | 10.0 | 15.1 | 60 | 94 | 94 | 40 | 2.35 | −15 |
| 3 | 1.8 | 10.2 | 79.8 | 0.1 | 1.7 | 88:12 | 1 | 10.0 | 15.1 | 16 | 94 | 94 | 11 | 8.5 | −15 |
| 4 | 1.1 | 9.2 | 82.3 | — | 1.9 | 90:10 | 1.01 | 10.0 | 15.2 | 32 | 94 | 95 | 21 | 4.4 | −15 |
| 5 | 1.0 | 12.0 | 63.7 | — | 0.4 | 84:16 | 1 | 27.0 | 36.0 | 19 | 255 | .225 | 13 | 20.1 | −15 |
| 6 | 1.6 | 9.0 | 87.6 | 0.3 | 1.3 | 90:10 | .85 | 8.5 | 11.0 | 27 | 80 | 68 | 18 | 4.4 | −15 |
| 7 | 1.5 | 8.1 | 89.6 | 0.15 | 0.8 | 92:8 | .78 | 70.0 | 82.1 | 385 | 660 | 514 | 257 | 2.6 | −15 |
| 8 | 1.3 | 8.0 | 77.9 | — | 0.8 | 91:9 | .805 | 67.0 | 81.3 | 381 | 632 | 509 | 254 | 2.5 | −15 |
| 9 | 2.0 | 9.6 | 86.9 | — | 1.0 | 90:10 | .75 | 8.0 | 9.0 | 62 | 75 | 56 | 41 | 1.8 | 0 |
| 10 | 3.2 | 10.2 | 84.5 | — | 1.0 | 89.11 | .47 | 10.0 | 7.0 | 53 | 94 | 44 | 35 | 2.7 | 20 |